United States Patent [19]

Yamamoto

[11] Patent Number: 4,900,316
[45] Date of Patent: Feb. 13, 1990

[54] VACUUM SKIN CLEANER

[75] Inventor: Masuo Yamamoto, Habikino, Japan

[73] Assignee: Azz International Co., Ltd., Osaka, Japan

[21] Appl. No.: 109,831

[22] Filed: Oct. 16, 1987

[30] Foreign Application Priority Data

Oct. 18, 1986 [JP] Japan ................................ 61-247850

[51] Int. Cl.⁴ .............................................. A61M 1/00
[52] U.S. Cl. ..................................... 604/313; 239/310
[58] Field of Search ................... 604/77, 118, 119, 73, 604/74, 902, 313–316, 62 A; 128/62 A; 433/80, 91; 285/8, 404; 15/409; 239/47, 48, 310, 318, 403

[56] References Cited

U.S. PATENT DOCUMENTS

| | | | |
|---|---|---|---|
| 733,881 | 7/1903 | Smith | 285/8 |
| 948,005 | 2/1910 | Campbell | 604/315 |
| 1,080,420 | 12/1913 | Clifton | 15/409 |
| 1,196,344 | 8/1916 | Florez | 604/315 |
| 3,227,380 | 1/1966 | Pinkston | 128/62 A |
| 3,808,631 | 5/1974 | Shibata et al. | 15/409 |
| 3,964,484 | 6/1976 | Reynolds et al. | 604/902 |
| 4,540,406 | 9/1985 | Miles | 604/902 |

FOREIGN PATENT DOCUMENTS

| | | | |
|---|---|---|---|
| 0836360 | 1/1939 | France | 604/313 |
| 0137886 | 5/1930 | Switzerland | 604/313 |

*Primary Examiner*—Jerome L. Kruter
*Attorney, Agent, or Firm*—Birch, Stewart, Kolasch & Birch

[57] ABSTRACT

A vacuum skin cleaner includes a negative pressure generator and an applicator cap, wherein the negative pressure generator has an internal venturi water passage and a suction passage. One end of the water passage of the negative pressure generator is connected to a tap water faucet and has a discharge opening at its other end. The suction passage communicates with a throat of the venturi water passage, and the applicator cap communicates with the suction passage and has a mouth opening for making contact with the human skin.

15 Claims, 3 Drawing Sheets

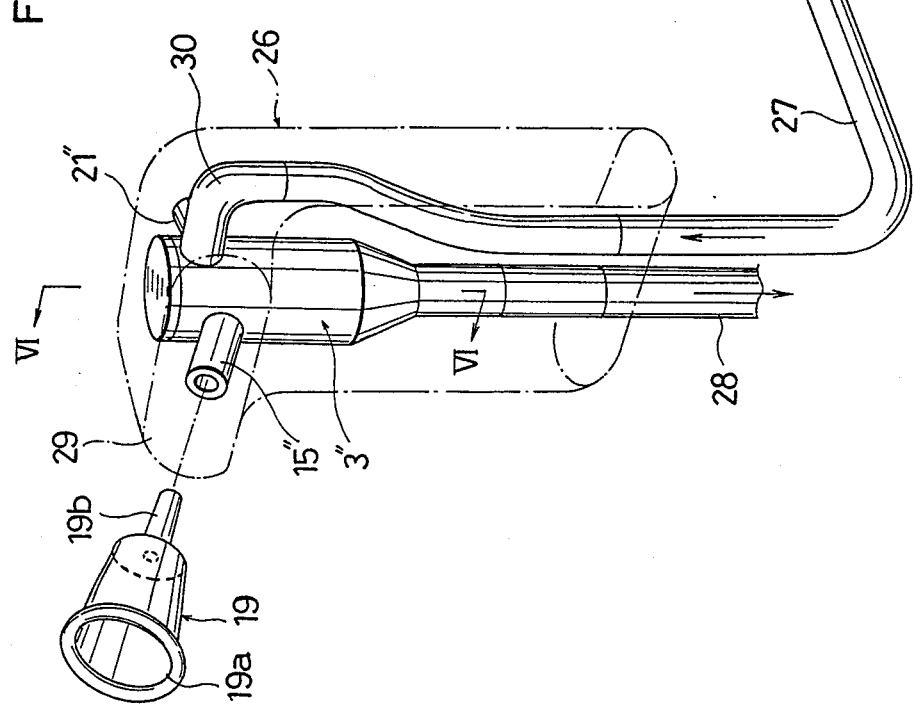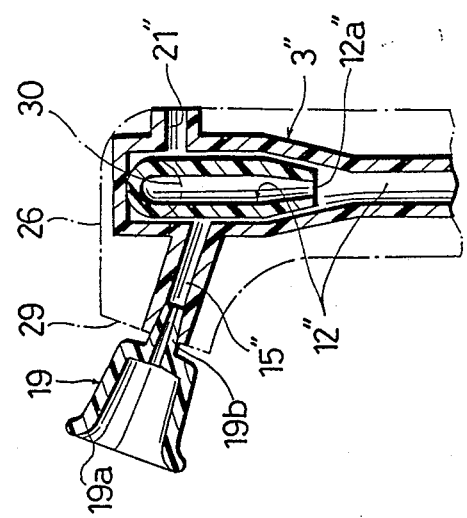

VACUUM SKIN CLEANER

BACKGROUND OF THE INVENTION

1. Field of the Invention:

This invention relates to a vacuum skin cleaner which is used to suck out various wastes, such as metabolic wastes, cosmetic residues, dust, and so on, accumulated within the human skin pores.

2. Description of the Prior Art:

It is well known that to maintain the human skin in good condition it is not only required to remove an aged horny layer, but it is also required that the metabolism for producing a new horny layer and to improve secretion of sebum, in order to always maintain the human skin in good condition. Particularly, the sebum, which is secreted through the skin pores, is known to be superior in skin protection and refinement to any artificial skin conditioners.

As a result of the daily routines of life or as a result of makeup, various wastes, such as metabolic wastes, cosmetic residues, dust and so on, may accumulate within and clog up the skin pores, thereby impeding sebum secretion. Further, such wastes can also hinder skin respiration (dermal respiration) thereby reducing metabolism in addition to causing annoying pimples, blackheads and rashes. In view of skin care, it is thus absolutely necessary to remove the wastes which clog the pores by some method.

Face washing with known face cleansers is considered very effective by temporarily keeping the face clean. However, such face washing is insufficient in that it fails to remove various wastes which have already accumulated within the skin pores. Further, the face cleansers have a vital disadvantage in that in addition to cleansing the skin, the cleaners wash away the secreted sebum itself.

A vacuum skin cleaner is commercially available which comprises a negative pressure generator connected to an applicator cap. The negative pressure generator incorporates a vacuum pump driven by an electric motor.

In operation, the applicator cap which is put under vacuum is pressed against the human skin to forcibly suck out pore clogging wastes and to stimulate the skin for enhancing metabolism. Such suction cleaning is now widely adopted particularly in beauty parlors or salons.

However, since the conventional vacuum skin cleaner operates electrically, it is disadvantageous in the following four disadvantages.

First, the conventional cleaner cannot be operated safely where water is used because the user may receive an accidental electrical shock. This means that suction skin cleaning cannot be conducted during or immediately after washing the face or taking a bath. The electric cleaner, even if completely sealed against water, will still have a problem of short service life in addition to involving a high production cost.

In fact, suction cleaning can be done easily when the skin is wet with water because of smooth contaact between the applicator cap and skin caused by the water, particularly when the skin is warm as a result of taking a bath, the skin pores are fully open to the conventional cleaner at such an appropriate time.

Secondly, the electric vacuum skin cleaner provides poor adjustability of the suction force created. More specifically, th electric motor driving the cleaner provides only a "ON" or "OFF" state or at most stepwise suction adjustment (e.g. "LOW" and "HIGH"). Thus, it is impossible with the conventional cleaner to achieve minute suction adjustment depending on various requirements (e.g. particular condition or portion of the skin, user's taste, etc.).

Thirdly, it is difficult with the conventional cleaner to wash away the wastes which have collected on the applicator cap and/or in the suction passage. Thus, the cleaner may get unacceptably dirty or sometimes inoperative due to clogging up of the suction passage after repeated use.

Finally, it is uncomfortable to use the conventional cleaner because of motor vibration and noises.

SUMMARY OF THE INVENTION

It is an object of the present invention to provide a vacuum skin cleaner which is safely and comfortably usable with water, steplessly adjustable in suction force, and capable of being always kept clean.

Another objective of the invention is to provide a vacuum skin cleaner which is easy to handle.

According to the present invention, there is provided a vacuum skin cleaner comprising a negative pressure generator having an internal water passage and a suction passage. The water passage is connected at one end to a tap water faucet and has a discharge opening at the other end, the water passage having a cross-sectionally reduced intermediate portion. The suction passage communicates the intermediate portion. An applicator cap is provided in the present invention for communicating with the suction passage and having an opening mouth for contact with the human skin.

Other objectives, features and advantages of the invention will be readily understood from the following description of the preferred embodiments given with reference to the accompanying drawings.

BRIEF DESCRIPTION OF THE DRAWINGS

In the accompanying drawings:

FIG. 5 is a perspective view of still another vacuum skin cleaner embodying the present invention; and FIG. 6 is a sectional view taken on lines VI—VIi in FIG. 5.

DETAILED DESCRIPTION OF THE PREFERRED EMBODIMENTS

Figure 1:
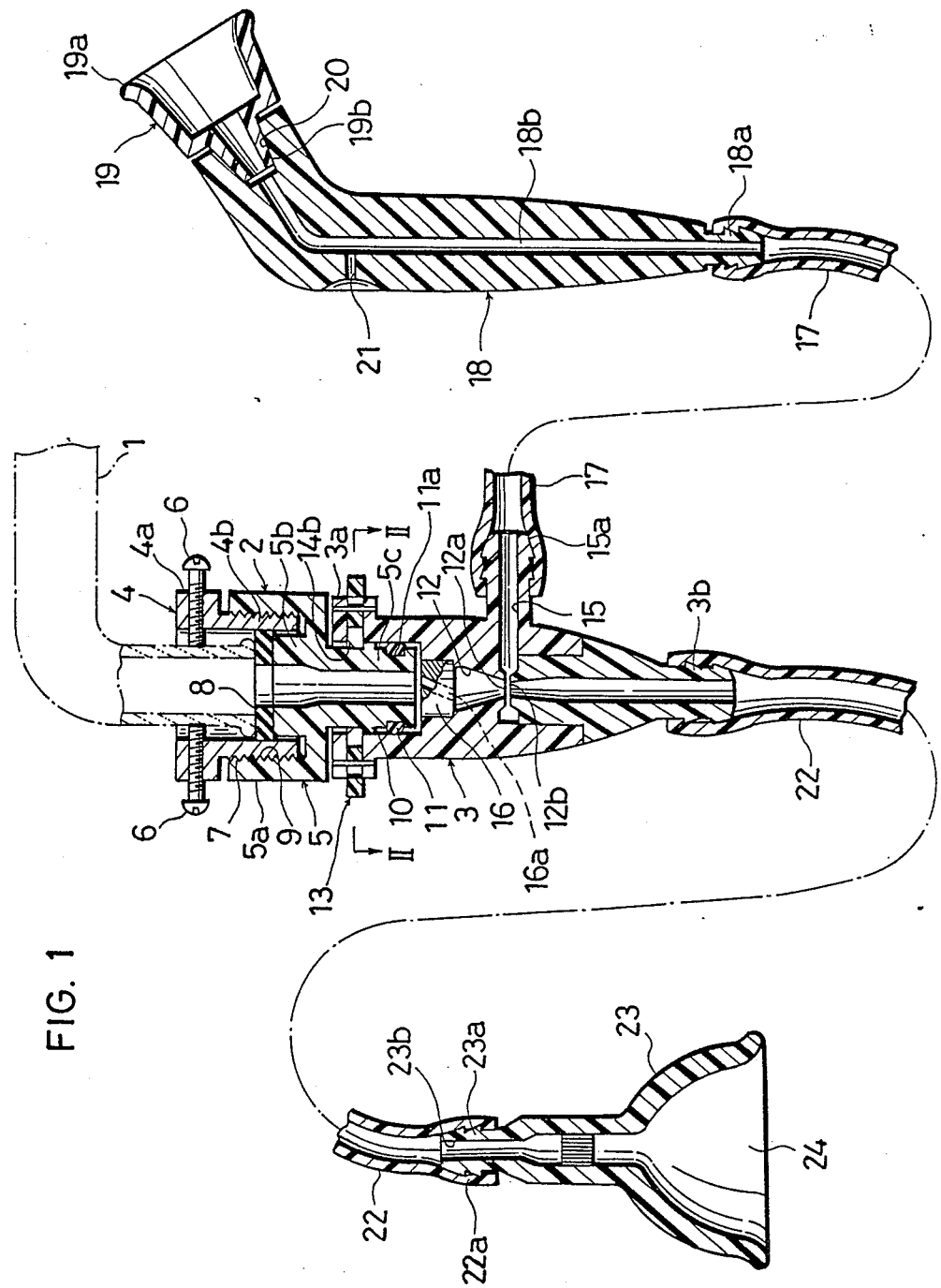
FIG. 1 is a view in vertical section of a vacuum skin cleaner embodying the present invention.

Throughout the accompanying drawings, like parts are referred to by the same reference numerals and characters to avoid duplication of explanation.

Referring now to FIG. 1 of the accompanying drawings, a vacuum skin cleaner according to a first embodiment of the present invention comprises a mounting attachment 2 detachably connected to a tap water faucet 1, and a negative pressure generator 3 which in turn is detachably connected to the attachment 2.

The mounting attachment 2 includes an upper member 4 connectable to the faucet 1. More specifically, the upper member 4 has an enlarged ring portion 4a surrounding the discharge end of the faucet 1, and a cylindrical screw portion 4b extending downward from the ring portion 4a and formed with external threads 7. A plurality (e.g. four) of equiangularly spaced set screws 6 extend radially inward through the ring portion 4a into contaact with the faucet discharge end for fixing the upper member 4 to the faucet 1. The screw portion 4b internally supports a sealing ring plate 8 below the faucet discharge end.

It should be appreciated that the upper member 4 can be fixed to a faucet discharge end of any cross section by independently advancing the set screws 6 into contact with the faucet discharge end.

The attachment 2 further includes a lower member 5 screwed to the upper member 4. More particularly, the lower member 5 has a cylindrical screw portion 5a which is formed with internal threads 9 for screw engagement with the screw portion 4b of the upper member 4 and a cylindrical connector portion 5c which is smaller in diameter than the screw portion 5a and extends downward for connection to the negative pressure generator 3.

The connector portion 5c has, as an integral upward extension thereof, a seal pressing portion 5b which is smaller in diameter than the cylindrical screw portion 4b of the upper member 4. Thus, upon screwing of the lower member 5 onto the uppr member 4, the seal pressing portion 5b presses the sealing ring plate 8 against the discharge end of the faucet 1 to provide water-tightness for the attachment 2 itself and for the connection between the faucet 1 and the attachment 2.

Further, the connector portion 5c is formed with an integral annular projection 10 and a annular groove 11a below the annular projection 10 for receiving an annular seal ring 11.

The negative pressure generator 3 internally defines a water passage 12 and has an upper cylindrical fitting portion 3a which is releasably mounted to the connector portion 5c of the lower attachment member 5 by means of a lock mechanism 13.

Figure 2:
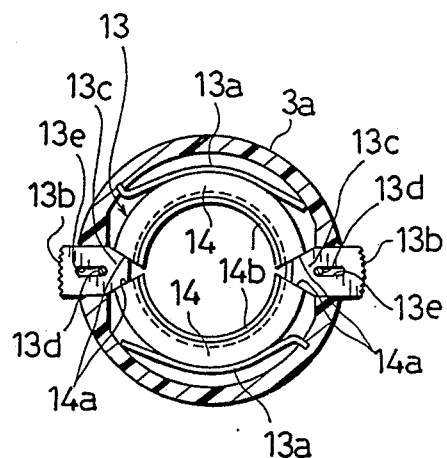
FIG. 2 is a sectional view taken on lines II—II in FIG. 1.

As best illustrated in FIG. 2, the lock mechanism 13 comprises a pair of semicircular stopper segments 14 which together form a substantially annular body and are urged toward each other by a pair of springs 13a. Each stopper segment 14 has end faces 14a which are opposed to and spaced from the corresponding end faces 14a of the other stopper segment 14 to define a pair of V-shaped gaps. Both stopper segments 14 respectively have upper inner circumferential edges 14b which are chamfered to form, in combination, a substantially conical surface.

The lock mechanism 13 further includes a pair of release buttons 13b which radially extend through the cylindrical fitting portion 3a of the negative pressure generator 3 at a pair of diametrically opposite positions thereof. Each button 13b has a wedge head 13c which fits into a corresponding V-shaped gap between the two stopper segments 14. Thus, when the buttons 13b are advanced by finger pressure, the stopper segments 14 are forcibly moved away from each other against the urging force of the springs 13a due to wedging effect between the wedge heads 13c of the respective buttons 13b and the gap forming end faces 14a of the stopper segments 14. When the buttons 13b are freed from pressure, the stopper segments 14 are automatically displaced toward each other by the restoring force of the springs 13a with resultant retraction of the buttons 13b. The retracting movement of each button 13b is restrained by a pin 13d which fits in a radial slot 13e formed in the button 13b.

For mounting the negative pressure generator 3 to the attachment 2, the upper cylindrical portion 3a of the generator 3 is forcibly fitted from below onto the connector portion 5c of the attachment lower member 5. Upon contact of the stopper segments 14 with the annular projection 10 of the attachment lower member 5, the chamfered edges 14b of the stopper segments 14 function to move the segments 14 away from each other against the biasing force of the springs 13a, thereby permitting the segments 14 to ride over and engage with the annular projection 10. At this time, the seal ring 11 comes into sealing contact with the inner circumferential surface of the upper cylindrical portion 3a to provide water-tightness between the attachment 2 and the negative pressure generator 3.

For removing the generator 3 from the attachment 2, the release buttons 13b are pushed to move the stopper segments 14 away from each other, and the generator 3 is pulled downward.

The water passage 12 formed within the negative pressure generator 3 is provided in the form of a well known venturi, the diameter of which increases progressively in opposite directions from its smallest diameter portion or throat 12a. The venturi passage 12 is formed at the smallest diameter portion 12 with an annular slit 12b which communicates with a laterally extending suction nose 15 having an inlet connection end 15a.

According to the preferred embodiment illustrated in FIG. 1, the venturi passage 12 is provided at its inlet end with a flow rectifying member 16 which has a plurality (only one shown) of inclined through-bores 16a. The rectifying member 16 imparts a whirling motion to the flowing water to maximize vacuum production at the smallest diameter portion 12a. Obviously, the rectifying member 16 may be modified to have a plurality of screw blades (not shown) instead of the inclined through-bores 16a.

The inlet end 15a of the suction nose 15 is connected to an outlet end 18a of a grip member 18 by a flexible hose 17. The grip member 18 has an air passage 18b extending through it and is formed at its inlet end with a tapered mounting hole 20. The grip member 18 is further provided with a vacuum relief port 21 which communicates with an intermediate portion of the air passage 18b.

The grip member 18 has such a shape as to provide ready gripping and is used to exchangeably mount an applicator cap 19 having an opening mouth 19a for contact with the human skin. More specifically, the cap 19 has a tapered projection 19b which is fitted into the tapered mounting hole 20 of the grip member 18.

Figure 3:
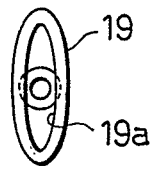
FIG. 3 is a plan view showing an example of an applicator cap.

According to the example illustrated in FIG. 3, the opening mouth 19a of the cap 19 is oval for facilitated application to portions of the human skin around the nose for example. However, the cap 19 may be replaced by another which is differently dimensioned and shaped depending on a particular portion or portions of the human skin to which it is applied. It should be noted in this connection that a suction force per unit area does not vary despite a change in the overall area of the cap mouth 19a.

The negative pressure generator 3 has a water discharge end 3b which is connected via a flexible hose 22 to a projecting base portion 23a of a washing attachment 23 which, according to the example illustrated in FIG. 1, is in the form of a cone. The conical washing attachment 23 defines a water outlet opening 24. It should be noted that the washing attachment 23 is connected to a discharge end 22a of the hose 22 only at the time of an washing operation but not at the time of suction cleaning.

In operation, the faucet 1 is turned on to supply tap water which flows through the flow rectifying member 16 and then through the venturi passage 12 to ultimately discharge through the hose 22 with the washing attachment 23 detached. Upon passage through the venturi throat 12a, the water flows at a maximum speed to develop a maximum dynamic pressure while providing a minimum static pressure according to the Bernoulli law. Since the static pressure at the discharge end 22a of the hose 22 is equal to an atmospheric pressure (zero gauge pressure), the static pressure at the venturi throat 12a becomes negative.

A user grasps the grip member 19 with the opening mouth 19a of the applicator cap 19 pressed against her (or his) intended facial spot and then closes the vacuum relief port 21 by a finger tip. As a result, the negative pressure at the venturi throat 12a is also applied to the particular facial spot enclosed by the cap opening mouth 19a to conduct desired suction cleaning of the spot.

Such suction cleaning may be effected over a wide range by moving the applicator cap 19 from one part to another part on the user's face. Further, it is also possible to clean the entire face by selectively using various applicator caps.

The negative pressure applied to the user's face may be steplessly adjusted by varying the flow rate of the tap water passing through the negative pressure generator 3 or by partially opening the vacuum relief port 21 to different degrees. The vacuum relief port 21 may be fully opened to interrupt the suction cleaning operation.

For practical purpose, it is recommended to use the skin cleaner of the present invention at the time of or immediately after taking a bath. This is because the skin pores are fully open due to heat to allow discharge. Suction cleaning of various eastes (metabolic wastes, cosmetic residues, dust, etc.) which have accumulated within the pores can be accomplished very easily at this time.

The wastes collected by the applicator cap 19 may be washed away by directing toward the cap 19 the water discharged through the hose 22. For this purpose, the washing attachment 23, which has a water passage 23b of reduced cross section, may be connected to the hose 22 to provide a more vigorous jet of water adapted for washing. It should be noted in this connection that a suitable amount of air is introduced through the suction nose 15 into the water discharged through the washing attachment 23 during such washing, and the introduced air forms minute bubbles which ultimately break with resultant production of ultrasonic waves to enhance washing effect.

Further, the washing attachment 23 may be pressed against the user's face after the above described suction cleaning to conduct washing thereof with comfortable massaging effect which results in accelerated blood circulation and metabolism. In this case, the conical washing attachment 23 also has an advantage of preventing water splash during such face washing.

Figure 4:
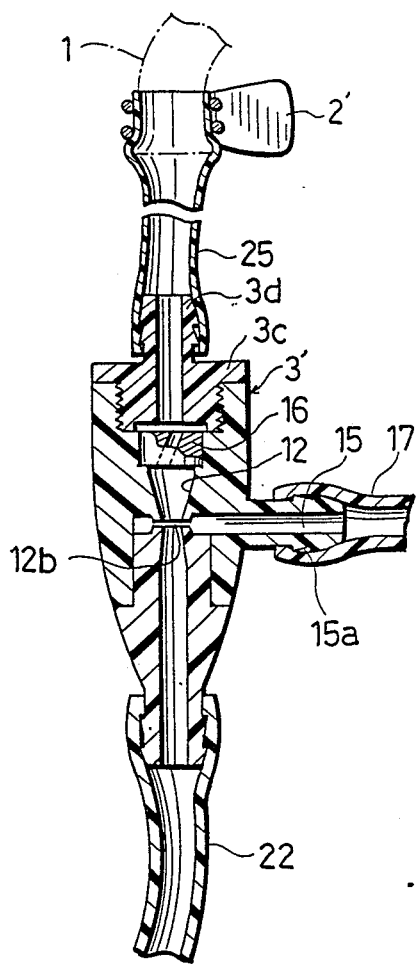
FIG. 4 is a view in vertical section of another vacuum skin cleaner embodying the present invention.

FIG. 4 illustrates a second embodiment of the present invention in which a negative pressure generator 3' is connected to a tap water faucet 1 by means of a vertically extending flexible hose 25. More specifically, the generator 3' has an upper closure member 3c integrally formed with an upward connector projection 3d which is connected to the lower end of the hose 25, whereas the upper end of the hose 25 is connected to the discharge end of the faucet 1 by means of an expandable clamp member 2'. Otherwise, the second embodiment is substantially identical in function and configuration to the first embodiment illustrated in FIG. 1.

According to a third embodiment of the present invention illustrated in FIGS. 5 and 6, a negative pressure generator 3" is accommodated in a casing 26 which serves as a grip member. The generator 3" has a water inlet connector 30 which is connected to one end of a relatively long flexible hose 27. The other end of the hose 27 is connected to the discharge end of a faucet 1 by means of an expandable clamp member 2".

As better illustrated in FIG. 6, the negative pressure generator 3" internally has a water passage 12" which is designed to produce a negative pressure at a minimum cross-sectional portion 12a". The portion 12a" communicates with a suction nose 15" extending forward to a foremost wall 29 of the casing 26 for directly receiving a tapered projection 19b of an applicator cap 19. The portion 12a" further communicates with a rearwardly extending vacuum relief port 21" which is closable by a finger.

The lower end of the negative pressure generator 3" or the water passage 12" is connected to a flexible hose 28 which in turn may be connected to a washing attachment (not shown) which is similar to the one illustrated in FIG. 1.

The vacuum skin cleaner according to the present invention requires no electric parts (motors, etc.), so that it can be operated very safely and washed clean with water after operation. Further, need for water supply makes the skin cleaner of the present invention particularly advantageous for use in a bath room (during or after taking a bath) where vacuum skin cleaning is considered most effective. Still further, the simplicity in construction of the skin cleaner reduces the possibility of malfunction and ensures a long service.

The present invention being thus described, it is obvious that the same may be further varied in many ways. For instance, the releasable lock mechanism 13 (FIG. 1) may be provided in the form of spring-biased balls or like elements which engage with and disengage from the annular projection 10 of the attachment lower member 5b in response to push and pull on the negative pressure generator 3, consequently obviating the buttons 13b. Further, the water discharge hose 22 (or 28) and the washing attachment 23 may be obviated. Such modifications are not to be regarded as a departure from the spirit and scope of the invention, and all such modifications as would be obvious to those skilled in the art are intended to be included within the scope of the following claims.

I claim:

1. A vacuum skin cleaner comprising:
   a negative pressure generator having an internal water passage and a suction passage;
   said water passage being connected at one end to a tap water faucet and having a discharge opening at the other end;
   said water passage having a cross-sectionally reduced intermediate portion;
   said suction passage communicating with said intermediate portion;

an applicator cap communicating with said suction passage and having an opening mouth for contact with human skin; and a mounting attachment for removably connecting said negative pressure generator to said faucet;

said mounting attachment including, a first annular seal interposed between said mounting attachment and said faucet, a second annular seal interposed between said mounting attachment and said negative pressure generator, an upper portion removably fixed to said faucet by a plurality of radially extending set screws, and a lower portion removably fitted into said negative pressure generator, said lower portion being formed with an annular projection; and a releasable lock mechanism positioned between aid mounting attachment and said negative pressure generator to engage with and disengage from said annular projection.

2. The vacuum skin cleaner as defined in claim 1, wherein said lock mechanism comprises spring-based engaging elements which are radially movable for engagement with and disengagement from said annular projection of said attachment lower portion.

3. A vacuum skin cleaner comprising:

a negative pressure generator having an internal water passage and a suction passage;

said water passage being connected at one end to a tap water faucet and having a discharge opening at the other end;

said water passage having a cross-sectionally reduced intermediate portion;

said suction passage communicating with said intermediate portion; and an applicator cap communicating with said suction passage and having an opening mouth for contact with the human skin;

said water passage of said negative pressure generator is provided, at a position upstream from said cross-sectionally reduced intermediate portion, with a flow rectifying member means for imparting a whirling motion to water.

4. The vacuum skin cleaner as defined in claim 3, wherein said negative pressure generator is removably connected to said faucet by means of a mounting attachment, a first annular seal is interposed between said attachment and said faucet, and a second annular seal is interposed between said attachment and said generator.

5. The vacuum skin cleaner as defined in claim 4, wherein said mounting attachment has an upper portion removably fixed to said faucet by a plurality of radially extending set screws, and said mounting attachment further has a lower portion removably fitted into said negative pressure generator.

6. The vacuum skin cleaner as defined in claim 5, wherein said lower portion of said mounting attachment is formed with an annular projection, and a releasable lock mechanism is provided between said attachment and said negative pressure generator to engage with and disengage from said annular projection.

7. The vacuum skin cleaner as defined in claim 3, wherein said negative pressure generator is connected to said faucet by means of a hose.

8. The vacuum skin cleaner as defined in claim 3, wherein said water passage is in the form of a venturi passage progressively increasing in cross section from a venturi throat at which said cross-sectionally reduced portion is located.

9. The vacuum skin cleaner as claimed in claim 3, wherein said grip member is formed with a recess located at the position of said vacuum relief port for facilitation closing of aid vacuum relief port.

10. The vacuum skin cleaner as claimed in claim 3, wherein said grip member has a tapered mounting hole, and said applicator cap has a tapered mounting projection detachably fitted into said tapered mounting hole.

11. The vacuum skin cleaner as defined in claim 3, wherein said applicator cap is connected to said suction passage by means of a hose.

12. The vacuum skin cleaner as defined in claim 11, wherein said applicator cap is exchangeably mounted to a grip member having an air passage communicating with said hose.

13. The vacuum skin cleaner as defined in claim 12, wherein said grip member is formed with a closable vacuum relief port communicating with said air passage.

14. The vacuum skin cleaner as defined in claim 3, wherein said discharge opening of said water passage is connected to a detachable washing attachment by means of a hose.

15. The vacuum skin cleaner as defined in claim 3, wherein said lock mechanism comprises spring-biased engaging elements which are radially movable for engagement with and disengagement from said annular projection of said attachment lower portion.

* * * * *